United States Patent
Huddleston, III

(10) Patent No.: US 8,551,145 B2
(45) Date of Patent: Oct. 8, 2013

(54) ANTERIOR ADHERENT THORACOLUMBAR SPINE PLATE

(75) Inventor: Paul M. Huddleston, III, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1023 days.

(21) Appl. No.: 12/096,959

(22) PCT Filed: Dec. 19, 2006

(86) PCT No.: PCT/US2006/048475
§ 371 (c)(1),
(2), (4) Date: Jun. 11, 2008

(87) PCT Pub. No.: WO2007/075715
PCT Pub. Date: Jul. 5, 2007

(65) Prior Publication Data
US 2008/0294201 A1     Nov. 27, 2008

Related U.S. Application Data

(60) Provisional application No. 60/751,539, filed on Dec. 19, 2005.

(51) Int. Cl.
*A61B 17/80* (2006.01)
(52) U.S. Cl.
USPC .......................................... 606/283; 606/280
(58) Field of Classification Search
USPC ........... 623/17.11–17.16; 606/280, 283–286, 606/298–299, 70–71
See application file for complete search history.

(56) References Cited

U.S. PATENT DOCUMENTS

| 4,388,921 | A | * | 6/1983 | Sutter et al. ..................... 606/71 |
| 5,324,290 | A | | 6/1994 | Zdeblick et al. |
| 5,486,176 | A | | 1/1996 | Hildebrand et al. |
| 5,601,553 | A | | 2/1997 | Trebing et al. |

(Continued)

FOREIGN PATENT DOCUMENTS

| WO | 9747251 | 12/1997 |
| WO | 0141663 | 6/2001 |

OTHER PUBLICATIONS

PCT/US2006/048475 International Search Report and Written Opinion of the International Searching Authority.

(Continued)

*Primary Examiner* — Kevin T Truong
*Assistant Examiner* — Melissa A Hall
(74) *Attorney, Agent, or Firm* — Quarles & Brady LLP

(57) ABSTRACT

The implant is a fixation device shaped in the form of a plate for use in the fixation and stabilization of the thoracolumbar spine. The design and the configuration of the device allows for an anatomic fit of the plate in the spine. The improved fixation allows for an anatomical and biomechanicat advantage in stabilizing thoracolumbar spine trauma both in a primary fashion and/or in conjunction with vertebral body replacement. Its anatomic design allows the application of an ingrowth surface at the host/implant interface and encourages an additional point of fixation in cases at high risk for delayed or non-union such as severe trauma or malignancy. The thoracolumbar spine plate is anatomically designed to fit snugly against the thoracolumbar vertebral bodies through a twist around the Z (longitudinal) axis of the generally rectangular plate.

30 Claims, 5 Drawing Sheets

(56) References Cited

U.S. PATENT DOCUMENTS

| | | | |
|---|---|---|---|
| 5,603,713 | A | 2/1997 | Aust et al. |
| 6,193,721 | B1 | 2/2001 | Michelson |
| 6,228,085 | B1* | 5/2001 | Theken et al. ............... 606/289 |
| 6,398,783 | B1 | 6/2002 | Michelson |
| 6,602,257 | B1* | 8/2003 | Thramann ................ 606/86 B |
| 6,786,909 | B1 | 9/2004 | Dransfeld et al. |
| 7,074,221 | B2 | 7/2006 | Michelson |
| 2002/0183752 | A1* | 12/2002 | Steiner et al. ................ 606/69 |
| 2004/0116930 | A1* | 6/2004 | O'Driscoll et al. ............ 606/69 |
| 2004/0210217 | A1 | 10/2004 | Baynham et al. |
| 2005/0149026 | A1 | 7/2005 | Butler et al. |
| 2005/0246021 | A1* | 11/2005 | Ringeisen et al. ......... 623/17.11 |

OTHER PUBLICATIONS

The Titanium Anterior Thoracolumbar Locking Plate System Technique Guide. Synthes Spine, 1994.
http://www.sofamordanek.com/patient-vantage.html—Spinal Technologies, Vantage. Feb. 2004.
http://www.depuyacromed.com/products/thoracolumbartrauma/m2_anterior.asp—Depuy Spine, Inc. Products. Dec. 2005.
http://www.depuyacromed.com/products/thoracolumbartrauma/anteriorexpedium.asp—Depuy Spine, Inc. Products. Dec. 2005.
http://www.depuyacromed.com/products/thoracolumbartrauma/profile_anterior.asp—Depuy Spine, Inc. Products. Dec. 2005.
Trinica and Trinica Select Anterior Cervical Plate Systems. Zimmer Spine, Inc. 2005.

* cited by examiner

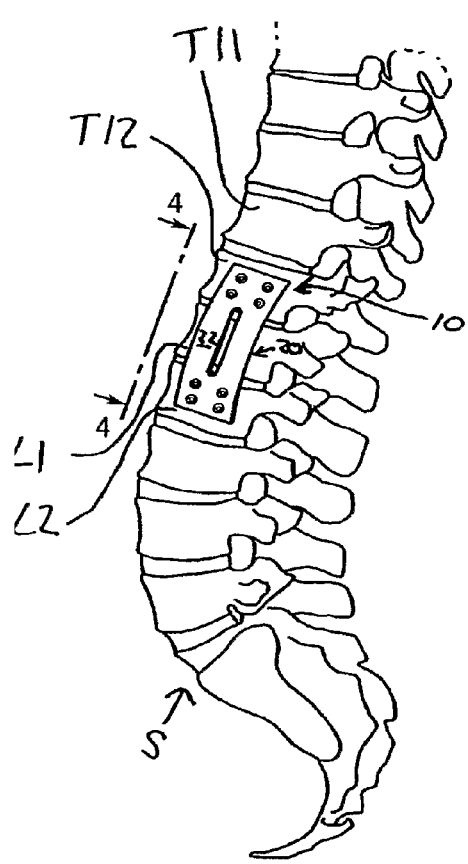
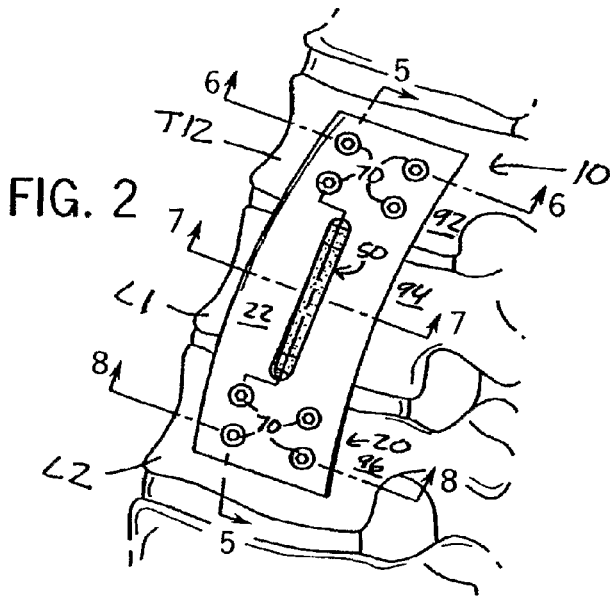
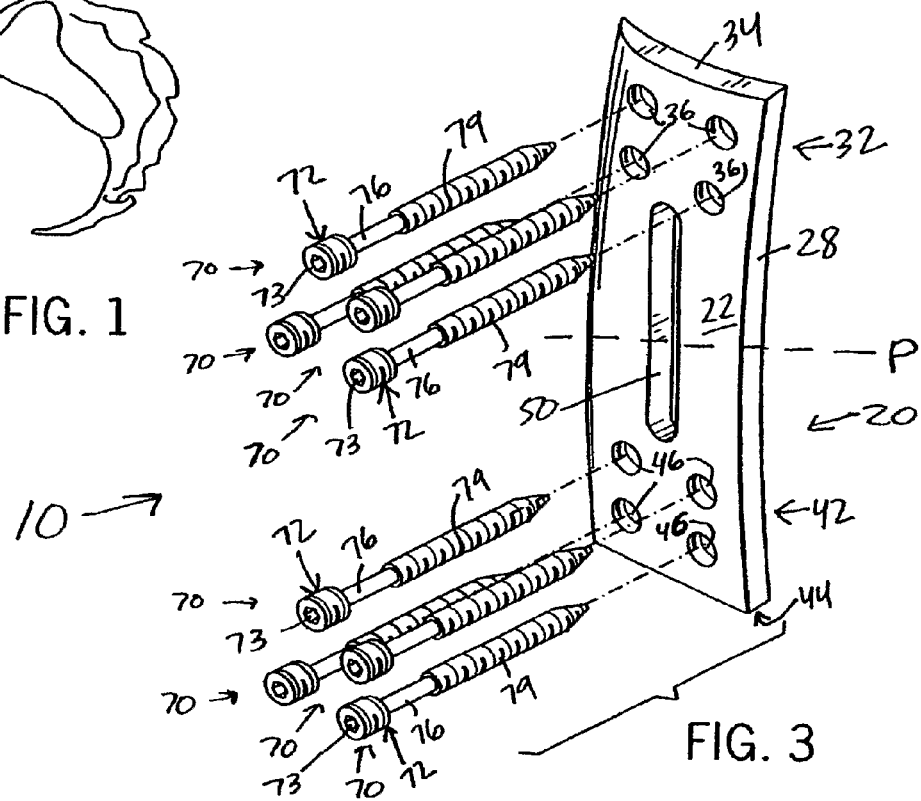
FIG. 1
FIG. 2
FIG. 3

ANTERIOR ADHERENT THORACOLUMBAR SPINE PLATE

CROSS-REFERENCES TO RELATED APPLICATIONS

This application claims priority from U.S. Provisional Patent Application No. 60/751,539 filed Dec. 19, 2005.

STATEMENT REGARDING FEDERALLY SPONSORED RESEARCH

Not Applicable.

BACKGROUND OF THE INVENTION

1. Field of the Invention

The present invention relates to devices for the anterior fixation of the spine. In particular, the present invention relates to an anterior adherent plate for the fixation of thoracic and lumbar vertebra.

2. Description of the Related Art

Trauma, burst fractures (typically in the T11, T12, L1 or L2 vertebrae), tumors, severe disc degeneration, and anterior fusion following multiple posterior operations are some of the causes of anterior thoracolumbar spinal instability. Anterior treatment of thoracolumbar spinal instability typically involves the use of anterior fixation devices including (i) connective structures, such as rods or plates, that extend between the vertebrae, and (ii) fasteners that engage the appropriate vertebra to affix the connective structures to the vertebra.

Current anterior fixation devices allow for semi-rigid stabilization through rod and staple constructs, or rigid immobilization with locking plate/screw devices. Various devices suitable for anterior thoracolumbar fixation are known. U.S. Pat. Nos. 6,228,085, 5,603,713, 5,601,553, 5,486,176 and 5,324,290 and U.S. Patent Application Publication No. 2004/0210217 describe bone fixation systems which include a plate and screws. Synthes® sells an anterior thoracolumbar locking plate system which employs a rigid screw and plate construct to form a locked plate. Medtronic® sells the Vantage™ anterior fixation system which includes a plate and screws. DepuySpine™ sells the M-2™ anterior plate system and the Profile® anterior fixation system which both include a plate and screws. DepuySpine™ also sells the Expedium™ spine system that utilizes a staple, screw and rod construct to provide a semi-rigid construct that enables a more custom fit of the implant. Its staple and screw interface allows a closer approximation of the implant to the spine but at the expense of more moving parts and less rigidity than a standard plate.

However, existing technologies may not provide rigid fixation and may not be appropriate for situations where there may be a need for prolonged rigid support such as in a milieu of delayed healing potential or severe spinal instability. Also, existing implants are non-anatomic and often only loosely approximate the patient anatomy resulting in a poor-fitting implant.

Accordingly, there is a need for an improved anterior plate for the fixation of thoracic and lumbar vertebra.

SUMMARY OF THE INVENTION

It has been clinically noted that the currently available anterior spine implants do not have an accurate anatomic design and fail to tightly conform to the changing vertebral body shapes in the spine. The inventor has quantitatively measured the decreasing anterior/posterior and increasing width in human male and female vertebrae as one progresses cranially to caudally in the thoracolumbar spine and used this information to create the anterior thoracolumbar plate of the present invention. The anterior thoracolumbar plate of the present invention has advantages over current devices for anterior fixation of thoracic and lumbar vertebra in that the present invention allows for a closer approximation of the anterior thoracolumbar plate to the host by the nature of its anatomic alignment. The addition of a compression hole to the anterior thoracolumbar plate facilitates the closest possible application of the anterior thoracolumbar plate. This closer fit of the anterior thoracolumbar plate to the spine shortens the moment arm of the construct and increases its overall stiffness.

The anterior thoracolumbar plate of the present invention is an anatomic spinal fixation device designed to stabilize the traumatized or reconstructed thoracolumbar spine. Its application on the anterior spine allows the stabilization and early mobilization of the patient with thoracolumbar fracture without the need for a posterior spinal operation. This invention addresses the problem of progressive deformity and implant or host failure by allowing both a compressive and rigid fixation.

In an example embodiment, the invention is a low profile anterior thoracolumbar spine plate comprised at the bone interface of porous tantalum. The thoracolumbar spine plate is anatomically designed to fit snugly against the thoracolumbar vertebral bodies (T11, T12, L1, L2) through a twist around the Z (longitudinal) axis. The side of the plate not snugly fit against the vertebral bodies may be smooth. At each end of the plate, there may be four holes to accommodate locking screws set at an angle. The screws may be formed from porous tantalum. The middle of the plate is an oval graft window. The plate can optionally integrate a vertebral body spacer with screw holes to engage the spacer. The use of an anatomic plate, both as a buttress and an additional point of fixation, allows for more rigid and secure fixation of complex reconstructions, including high risk fractures, tumors and infections. Although the example embodiment is an anterior thoracolumbar plate, the same design principles (anatomic fit and bone side composition of a material that supports bone ingrowth) can apply to plates designed for use with other vertebra. Also, any material that allows bone ingrowth may be placed on the spine plate surface, and porous tantalum is merely an example bone ingrowth material.

Therefore, the invention provides an anteriorly attachable adherent vertebra fixation device. The device has an elongated plate including an outer surface, an inner surface opposite the outer surface, a first side surface extending between the inner surface and the outer surface, a second side surface extending between the inner surface and the outer surface, a first end surface extending between the inner surface and the outer surface and between the first side surface and the second side surface, and a second end surface extending between the inner surface and the outer surface and between the first side surface and the second side surface. The second side surface is opposite the first side surface, and the second end surface is opposite the first end surface. The inner surface and the outer surface may taper in width from the second end surface to the first end surface. The plate may comprise, or consist essentially of, a metallic, ceramic, polymeric, or composite material.

The inner surface of the elongated plate is curved and is concave. The plate may have a central elongated oblong or oval slot. The plate includes a first section on one side of a plane transverse to the inner surface, the outer surface, the first side surface and the second side surface. A Z (longitudinal) axis of the plate may be normal to the transverse plane. The first section terminates in the first end surface. The plate includes a second section on an opposite side of the transverse plane. The second section terminates in the second end surface. The first section of the elongated plate is twisted in a first direction in relation to the plane and the second section is twisted in a second direction in relation to the plane where the second direction is opposite to the first direction.

In one aspect of the invention, the first section of the elongated plate is twisted and the second section of the elongated plate is twisted such that a first transverse line on the inner surface of the first section of the elongated plate conforms to a first surface of a first vertebra and a second transverse line on the inner surface of the second section of the elongated plate conforms to a second surface of a second vertebra when the plate is placed in contact with the spine of a patient. Preferably, the first section is twisted and the second section is twisted such that a third transverse line on the inner surface between the first transverse line and the second transverse line conforms to a third surface of a third vertebra intermediate the first vertebra and the second vertebra when the plate is placed in contact with the spine of a patient. In one embodiment, the first end surface of the elongated plate is twisted from about 2 degrees to about 20 degrees in relation to the second end surface. In another embodiment, the first end surface of the elongated plate is twisted from about 2 degrees to about 10 degrees in relation to the second end surface. Typically, the first direction and the second direction are circular with respect to the plane.

The inner surface of the elongated plate preferably includes a material that allows bone ingrowth into the material. In one form, the inner surface includes a porous material that allows bone ingrowth into the material such as a porous metallic material having a network of interconnected pores distributed throughout the metallic material.

In an example embodiment, the inner surface has a generally rectangular periphery, and the outer surface has a generally rectangular periphery, and the plate has an average longitudinal length of 70 millimeters to 90 millimeters. Preferably, the plate has a longitudinal length such that the plate spans at least three vertebra when the plate is placed in contact with the spine of a human patient. The plate may have an average width of 20 millimeters to 30 millimeters, and an average thickness of 2 millimeters to 10 millimeters. In one form, the plate has a first thickness adjacent the first side surface that is less than a second thickness adjacent the second side surface. The first side surface may be curved toward the inner surface.

In one version of the invention, the first section of the elongated plate includes at least one first fastener hole, and the second section of the elongated plate includes at least one second fastener hole. The plate may be dimensioned such that each first fastener hole can line up with the T12 human vertebra and each second fastener hole can line up with the L2 human vertebra when the plate is placed in contact with the thoracolumbar region of the spine of a patient.

The device may include one or more first screws dimensioned to fit each first fastener hole, and one or more second screws dimensioned to fit each second fastener hole. Preferably, each screw includes an outer surface comprising a porous material such as a porous metallic material having a network of interconnected pores distributed throughout the metallic material. Preferably, one or more of the first screws is dimensioned to fit each first fastener hole, and one or more second screws is dimensioned to fit each second fastener hole, wherein each screw includes an outer surface comprising a material that allows bone ingrowth into the material.

The first section of the elongated plate may include a first fastener hole and a second fastener hole wherein the first fastener hole of the first section has a central axis angled with respect to a central axis of the second fastener hole of the first section. Preferably, the central axis of the first fastener hole of the first section is angled inward toward the central axis of the second fastener hole of the first section. The second section of the elongated plate may include a first fastener hole and a second fastener hole wherein the first fastener hole of the second section has a central axis angled with respect to a central axis of the second fastener hole of the second section. Preferably, the central axis of the first fastener hole of the second section is angled inward toward the central axis of the second fastener hole of the second section.

In one form, the device is a thoracolumbar fixation device, and the first section of the elongated plate is twisted and the second section of the elongated plate is twisted such that a first transverse line on the inner surface of the first section conforms to an outer surface of the T12 human vertebra and a second transverse line on the inner surface of the second section conforms to an outer surface of the L2 human vertebra when the plate is placed in contact with the spine of a patient. Preferably, the first section of the elongated plate is twisted and the second section of the elongated plate is twisted such that a third transverse line on the inner surface between the first transverse line and the second transverse line conforms to an outer surface of the L1 human vertebra when the plate is placed in contact with the spine of a patient.

In another aspect, the invention provides a method for the treatment of spinal instability. In the method, the first section of a device according to the invention is attached to a first vertebra; and the second section of a device according to the invention is attached to a second vertebra. For example, the first section of the elongated plate may be attached to the T12 human vertebra and the second section of the elongated plate may be attached to the L2 human vertebra to provide fixation of the vertebrae.

These and other features, aspects, and advantages of the present invention will become better understood upon consideration of the following detailed description, drawings, and appended claims.

BRIEF DESCRIPTION OF THE DRAWINGS

FIG. 1 is a left side elevational view of an anterior thoracolumbar fixation device according to the invention mounted on a spine.

FIG. 2 is detailed left side elevational view of the anterior thoracolumbar fixation device of FIG. 1.

FIG. 3 is an exploded perspective view of the anterior thoracolumbar fixation device of FIG. 1.

Like reference numerals will be used to refer to like parts from Figure to Figure in the following description of the drawings.

DETAILED DESCRIPTION OF THE INVENTION

Figure 4:
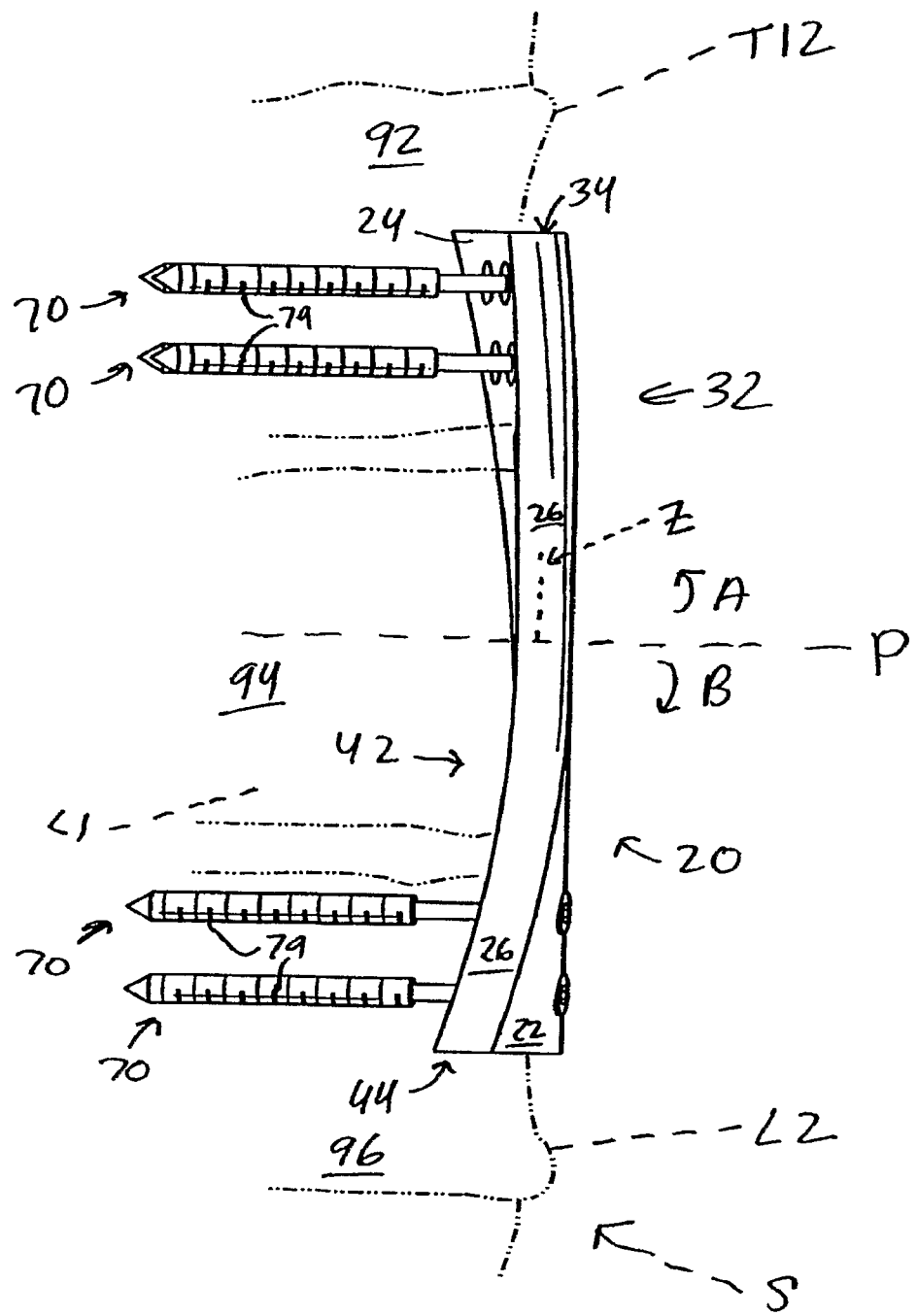
FIG. 4 is a front elevational view of the anterior thoracolumbar fixation device of FIG. 1 taken along line 4-4 of FIG. 1.

The present invention provides an anterior thoracolumbar fixation device designed to stabilize the traumatized or reconstructed thoracolumbar spine. Looking at FIGS. 1-8, the anterior thoracolumbar fixation device 10 includes an elongated generally rectangular plate 20. The plate 20 may be formed (such as by casting or machining) from a metal or metal alloy such as tantalum, tantalum alloys, titanium, titanium alloys (e.g., titanium-6-aluminum-4-vanadium), cobalt alloys, stainless steel alloys, or from a nonresorbable ceramic such as aluminum oxide or zirconia; or from a nonresorbable polymeric material such as polyethylene; or from a nonresorbable composite material such as a carbon fiber-reinforced polymer (e.g., polysulfone). The level of stabilization required may dictate the choice of material.

The plate 20 includes a generally rectangular outer surface 22, a curved and concave generally rectangular inner surface 24 opposite the outer surface 22, a first side surface 26 extending between the inner surface 24 and the outer surface 22, and a second side surface 28 extending between the inner surface 24 and the outer surface 22. The second side surface 28 is opposite the first side surface 26. A generally flat first end surface 34 extends between the inner surface 24 and the outer surface 22 and between the first side surface 26 and the second side surface 28. A generally flat second end surface 44 extends between the inner surface 24 and the outer surface 22 and between the first side surface 26 and the second side surface 28. The second end surface 44 and the first end surface 34 are at opposite longitudinal ends of the plate 20. The middle of the plate 20 has an oval graft window 50.

In one form, the plate 20 has an average longitudinal length (from the second end surface 44 to the first end surface 34) of 70 millimeters to 90 millimeters. Preferably, the plate 20 has a longitudinal length such that the plate 20 spans at least three vertebra (e.g., T12 to L2) when the plate is placed in contact with the spine of a patient. In one form, the plate 20 has an average width (from the first side surface 26 to the second side surface 28) of 20 millimeters to 30 millimeters. In one form, the plate 20 has an average thickness (from the inner surface 24 to the outer surface 22) of 2 millimeters to 10 millimeters. In another form, the inner surface 24 and the outer surface 22 taper in width from the second end surface 44 to the first end surface 34. In an example embodiment, the plate 20 has an average longitudinal length of 80 millimeters, an average width of 25 millimeters, and an average thickness of 7 millimeters of which 2 millimeters is porous surface material as described below.

Looking at FIGS. 2 and 4, the plate 20 includes a first section 32 on one side of a plane P transverse to the inner surface 24, the outer surface 22, the first side surface 26 and the second side surface 28. The first section 32 terminates in the first end surface 34. The plate 20 also includes a second section 42 on an opposite side of the plane P. The second section 42 terminates in the second end surface 44. As shown in FIG. 4, the first section 32 of the plate 20 is twisted in a first circular direction A (counterclockwise) in relation to the plane P and the second section 42 of the plate 20 is twisted in a second direction B (clockwise) in relation to the plane P. It can be seen that the second direction B is opposite to the first direction A in relation to the plane P and an upwardly directed Z axis normal to the plane P. Thus, the plate 20 has a twist around the Z axis as shown in FIG. 4. The degree of twist can vary. In one example, the first end surface 34 is twisted from 2 degrees to 20 degrees in relation to the second end surface 44. In another example, the first end surface 34 is twisted from 2 degrees to 10 degrees in relation to the second end surface 44. The Z twist in the plate 20 can also be seen by a comparison of FIGS. 6, 7 and 8.

Figure 6:
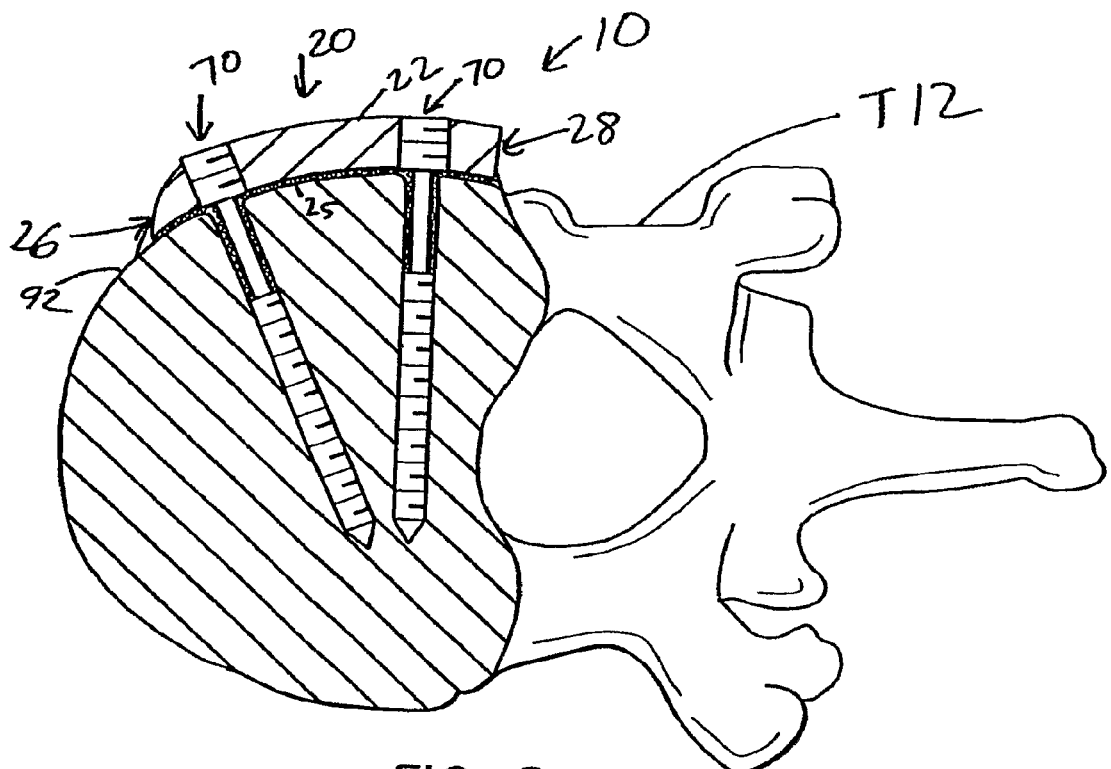
FIG. 6 is a cross-sectional view of the anterior thoracolumbar fixation device taken along line 6-6 of FIG. 2.
Figure 7:
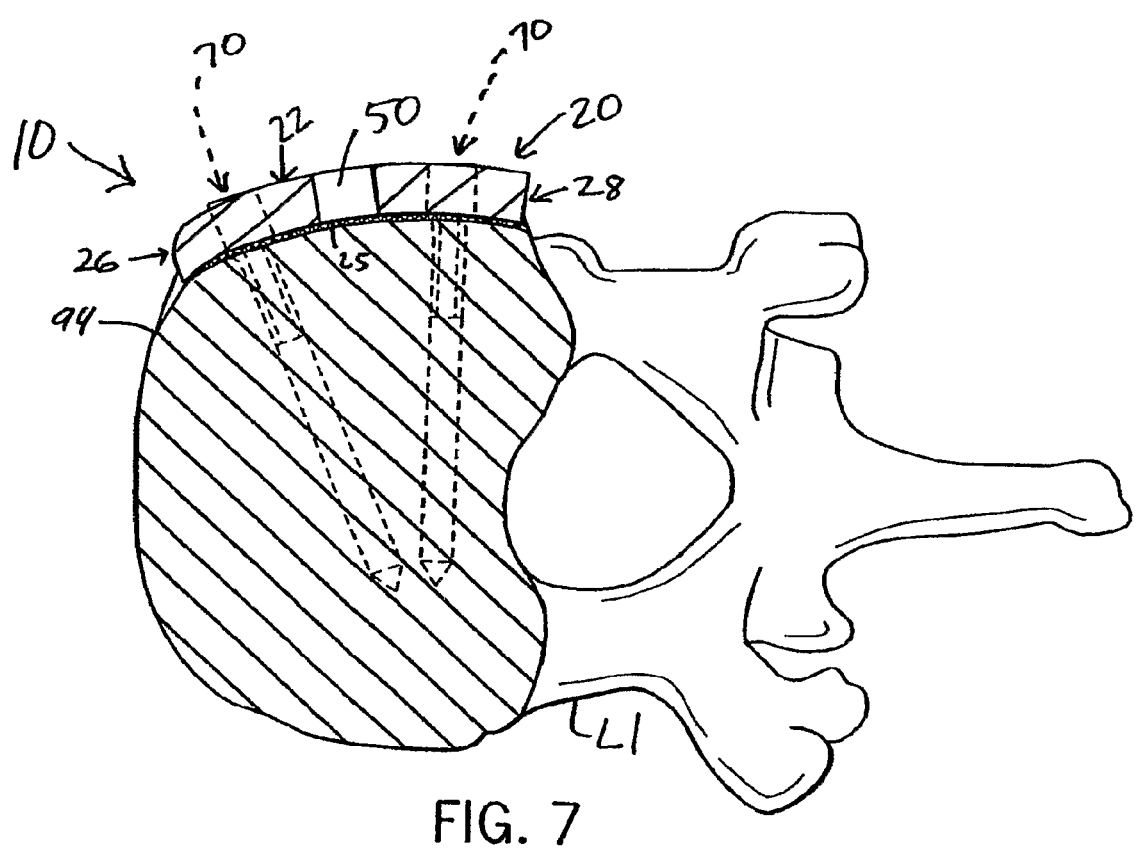
FIG. 7 is a cross-sectional view of the anterior thoracolumbar fixation device taken along line 7-7 of FIG. 2.
Figure 8:
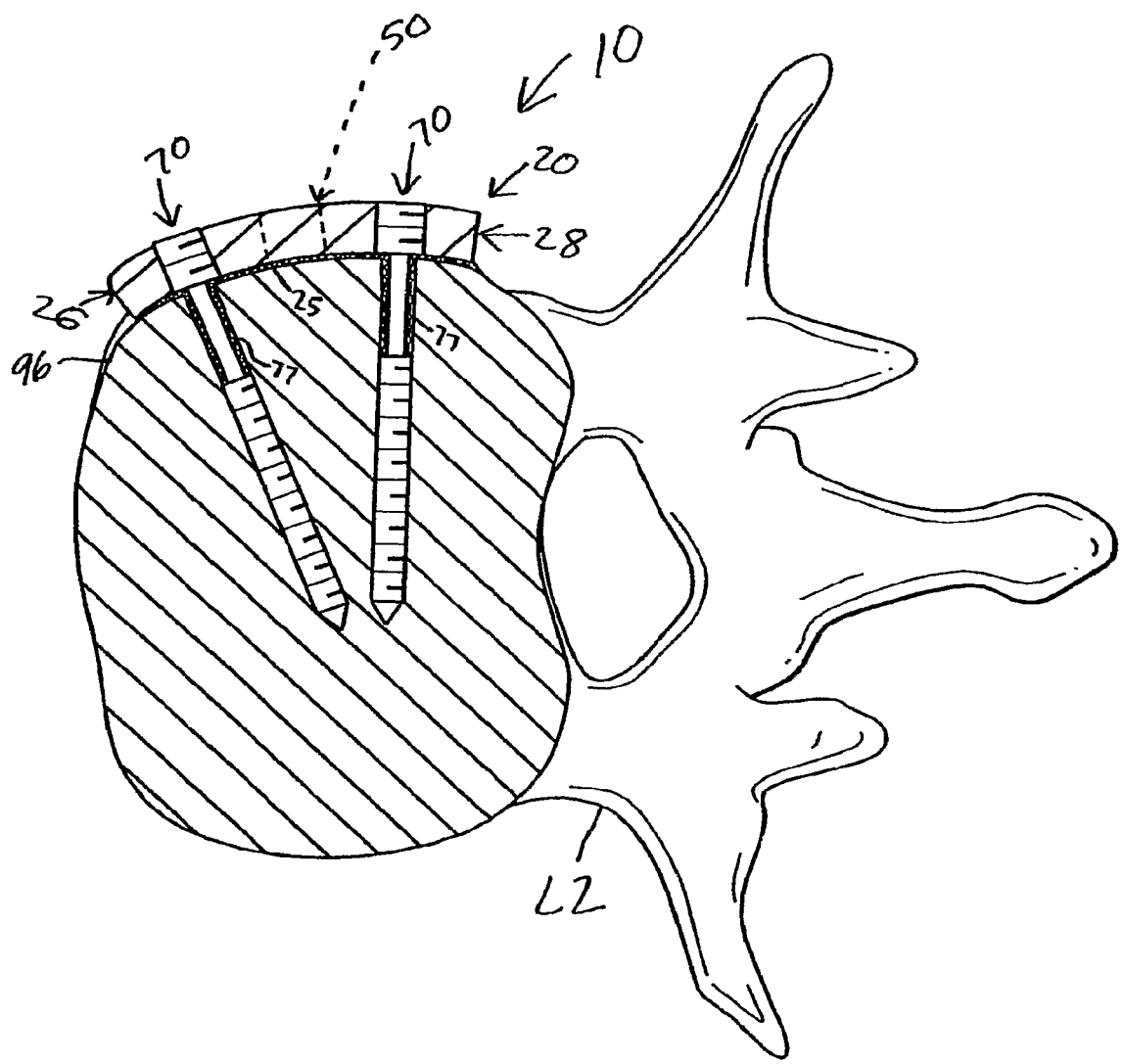
FIG. 8 is a cross-sectional view of the anterior thoracolumbar fixation device taken along line 8-8 of FIG. 2.

The first section 32 is twisted and the second section 42 is twisted such that a first transverse line from the first side surface 26 to the second side surface 28 on a section of the inner surface 24 within the first section 32 of the plate 20 conforms to surface 92 of the T12 vertebra. Also, a second transverse line from the first side surface 26 to the second side surface 28 on a section of the inner surface 24 of the second section 42 of the plate 20 conforms to a surface 96 of the L2 vertebra when the plate 20 is placed in contact with the spine S of a patient. Also, a third transverse line in plane P on the inner surface 24 of the plate 20 conforms to a surface 94 of the L1 vertebra when the plate 20 is placed in contact with the spine S of a patient. Thus, the plate 20 is anatomically designed to fit snugly against the thoracolumbar vertebral bodies T12, L1, L2 through a twist around the Z axis as shown in FIG. 4. The snug fit of the plate 20 against the T12 vertebra is shown in FIG. 6. The snug fit of the plate 20 against the L1 vertebra is shown in FIG. 7. The snug fit of the plate 20 against the L2 vertebra is shown in FIG. 8.

Figure 5:
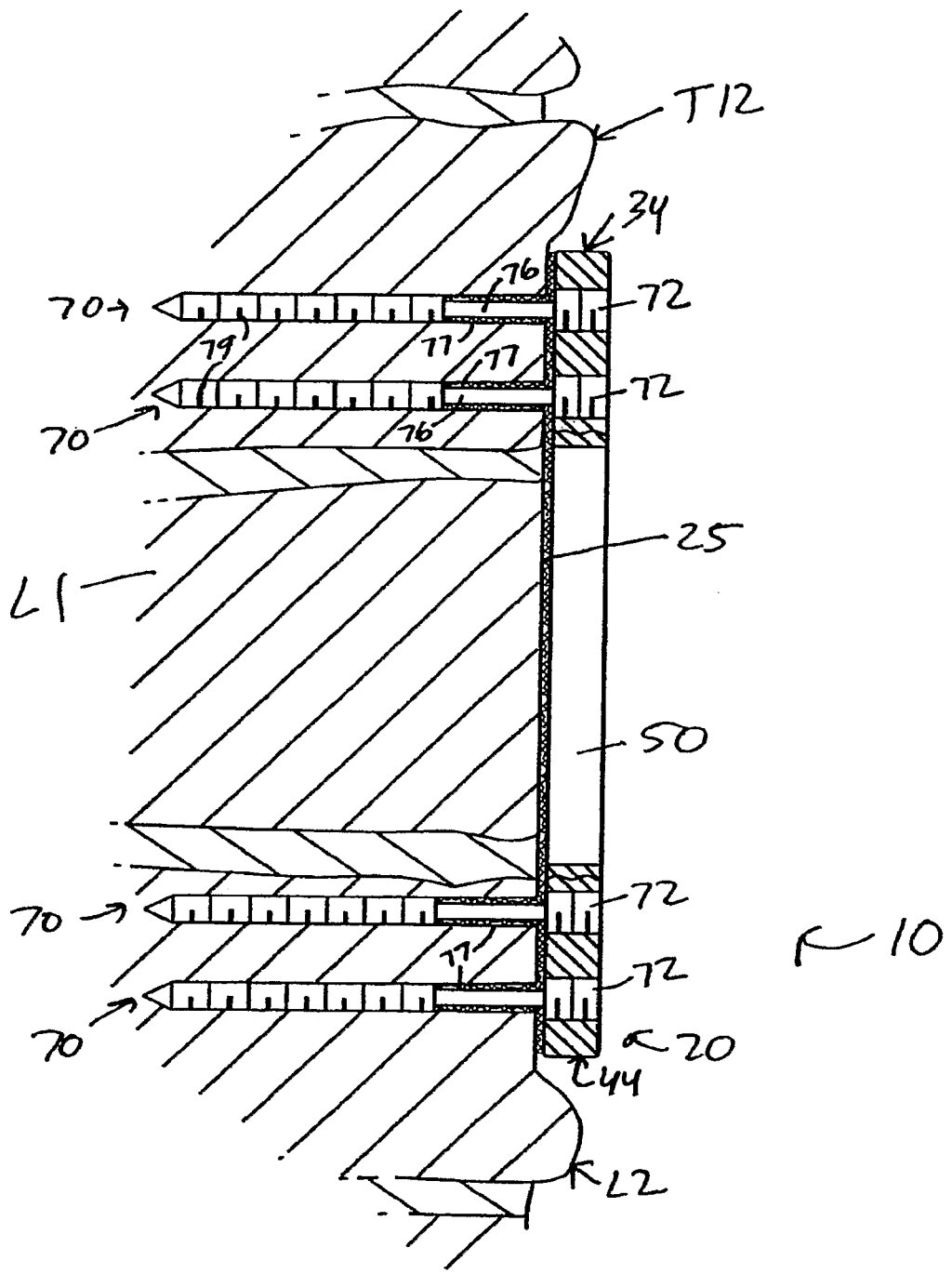
FIG. 5 is a cross-sectional view of the anterior thoracolumbar fixation device taken along line 5-5 of FIG. 2.

As shown in FIG. 5, the inner surface 24 of the plate 20 comprises a porous material 25. Preferably the porous material 25 comprises a porous metallic material having a network of interconnected pores distributed throughout the metallic material chosen to ensure that the resulting interstitial pore size is at least sufficient to permit bone tissue to grow into the porous material 25. Preferably, the metallic particles are formed from titanium, titanium alloys, cobalt alloys, stainless steel alloys, tantalum, tantalum alloys, and mixtures thereof. Various methods are known for forming the porous material on the inner surface, such as the methods described in U.S. Pat. Nos. 5,734,959, 4,206,516 and 3,855,638, which are incorporated herein by reference along with all other documents cited herein. However, the invention is not limited to these porous materials. Any material that permits bone tissue to grow into the material is suitable. The inner surface 24 of the plate 20 may also include a textured surface comprising a plurality of depressions such as grooves, dimples, or the like. Further, the inner surface 24 of the plate 20 may also have a coating of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof.

Looking at FIGS. 3-8, the plate 20 is secured to the anterior lateral section of the spine S using screws 70. Each screw may include a head 72 with an opening 73 for receiving a screw driver head, a shank portion 76, and a threaded portion 79. In FIGS. 5-8, there is shown a porous material 77 on the shank portion 76 of the screws 70. However, the porous material 77 may be on any surface of the screw 70. The porous material 77 preferably comprises a porous metallic material having a network of interconnected pores distributed throughout the metallic material chosen to ensure that the resulting interstitial pore size is at least sufficient to permit bone tissue to grow into the porous material 77. Preferably, the metallic particles are formed from titanium, titanium alloys, cobalt alloys, stainless steel alloys, tantalum, tantalum alloys, and mixtures thereof. Various methods are known for forming the porous material on the inner surface, such as the methods described in U.S. Pat. Nos. 5,734,959, 4,206,516 and 3,855,638. The screw 70 may also have a coating of a bone ingrowth promoting material such as hydroxyapatite ($Ca_{10}(PO_4)_6OH_2$), a calcium phosphate (e.g., tricalcium phosphate (Ca₃(PO₄)₂)), growth factors, bone morphogenic proteins, and mixtures thereof. The screws 70 are merely exemplary of a fastener suitable for affixing the plate 20 to the spine S. Other example fasteners include: partially threaded compression screws; and locking screws that are blunt, have a constant outside diameter, or have an increasing thread inside diameter. The screws 70 may be self tapping, or suitable pilot holes may be tapped in the spine before screw insertion. Also, the entire screw may be formed from a porous metallic material such as tantalum. A screw length of 30 to 35 millimeters is suitable.

When affixing the plate 20 to the spine S, the screws 70 are inserted through holes 36 in the first section 32 of the plate 20 and holes 46 in the second section 42 of the plate 20 as shown in FIG. 3. In one form of the plate 20, the plate 20 is dimensioned such that fastener holes 36 can line up with the T12 vertebra and fastener holes 46 can line up with the L2 vertebra when the plate 20 is placed in contact with the thoracolumbar region of the spine S of a patient. Angled insertion of the screws 70 as shown in FIGS. 6-8 is preferred, and the holes 36 and 46 may have their central axis inwardly angled in relation to the plate 20 to facilitate angled insertion of the screws 70.

Thus, the invention provides an anterior thoracolumbar plate that allows for a closer approximation of the anterior thoracolumbar plate to the host by the nature of its anatomic alignment. This closer fit of the anterior thoracolumbar plate to the spine shortens the moment arm of the construct and increases its overall stiffness. The anterior thoracolumbar spine plate is anatomically designed to fit snugly against the thoracolumbar vertebral bodies through a twist around the Z axis. The tight fit afforded by the anatomic design of the spine plate also allows for improved bone ingrowth into pores in the spine plate surface.

Although the present invention has been described in considerable detail with reference to certain embodiments, one skilled in the art will appreciate that the present invention can be practiced by other than the described embodiments, which have been presented for purposes of illustration and not of limitation. In particular, there has been described an anterior thoracolumbar plate; however, the same design principles (anatomic fit and bone side composition of a material that supports bone ingrowth) could apply to plates designed for use along the entire spine. Therefore, the scope of the appended claims should not be limited to the description of the embodiments contained herein.

INDUSTRIAL APPLICABILITY

The invention relates to an anterior adherent plate for the fixation of thoracic and lumbar vertebra.

What is claimed is:

1. An anterior vertebra fixation device comprising:
an elongated plate including an outer surface, an inner surface opposite the outer surface, a first side surface extending between the inner surface and the outer surface, a second side surface extending between the inner surface and the outer surface, the second side surface being opposite the first side surface, a first end surface extending between the inner surface and the outer surface and between the first side surface and the second side surface, and a second end surface extending between the inner surface and the outer surface and between the first side surface and the second side surface, the second end surface being opposite the first end surface,
wherein the inner surface is curved and is concave,
wherein the plate includes a first section on one side of a plane transverse to the inner surface, the outer surface, the first side surface and the second side surface, the first section terminating in the first end surface,
wherein the plate includes a second section on an opposite side of the plane, the second section terminating in the second end surface, and
wherein the first section is twisted in a first direction in relation to the plane and the second section is twisted in a second direction in relation to the plane, the second direction being opposite to the first direction, and
wherein the first section and the second section meet at the plane, and
wherein twisting in the first section begins at the plane and twisting in the second section begins at the plane.

2. The device of claim 1 wherein:
the first section is twisted and the second section is twisted such that a first transverse line on the inner surface of the first section conforms to a first surface of a first vertebra and a second transverse line on the inner surface of the second section conforms to a second surface of a second vertebra when the plate is placed in contact with the spine of a patient.

3. The device of claim 2 wherein:
the first section is twisted and the second section is twisted such that a third transverse line on the inner surface between the first transverse line and the second transverse line conforms to a third surface of a third vertebra intermediate the first vertebra and the second vertebra when the plate is placed in contact with the spine of a patient.

4. The device of claim 1 wherein:
the first end surface is twisted from 2 degrees to 20 degrees in relation to the second end surface.

5. The device of claim 1 wherein:
the first end surface is twisted from 2 degrees to 10 degrees in relation to the second end surface.

6. The device of claim 1 wherein:
the first direction and the second direction are circular with respect to the plane.

7. The device of claim 1 wherein:
the inner surface has a generally rectangular periphery, and the outer surface has a generally rectangular periphery.

8. The device of claim 1 wherein:
the inner surface comprises a material that allows bone ingrowth into the material.

9. The device of claim 1 wherein:
the inner surface comprises a porous material that allows bone ingrowth into the material.

10. The device of claim 1 wherein:
the inner surface comprises a porous metallic material having a network of interconnected pores distributed throughout the metallic material.

11. The device of claim 1 wherein:
the plate has an average longitudinal length of 70 millimeters to 90 millimeters.

12. The device of claim 1 wherein:
the plate has a longitudinal length such that the plate spans at least three vertebra when the plate is placed in contact with the spine of a patient.

13. The device of claim 1 wherein:
the plate has an average width of 20 millimeters to 30 millimeters.

14. The device of claim 1 wherein:
the plate has an average thickness of 2 millimeters to 10 millimeters.

15. The device of claim 1 wherein:
the plate has a first thickness adjacent the first side surface and a second thickness adjacent the second side surface, the first thickness being less than the second thickness.

16. The device of claim 1 wherein:
the plate has a central elongated slot.

17. The device of claim 1 wherein:
the inner surface and the outer surface taper in width from the second end surface to the first end surface.

18. The device of claim 1 wherein:
the first section includes at least one first fastener hole, and
the second section includes at least one second fastener hole.

19. The device of claim 18 wherein:
the plate is dimensioned such that each first fastener hole can line up with the T12 human vertebra and each second fastener hole can line up with the L2 human vertebra when the plate is placed in contact with the thoracolumbar region of the spine of a patient.

20. The device of claim 18 further comprising:
one or more first screws dimensioned to fit each first fastener hole, and
one or more second screws dimensioned to fit each second fastener hole,
wherein each screw includes an outer surface comprising a porous material.

21. The device of claim 20 wherein:
the porous material comprises a porous metallic material having a network of interconnected pores distributed throughout the metallic material.

22. The device of claim 18 further comprising:
one or more first screws dimensioned to fit each first fastener hole, and
one or more second screws dimensioned to fit each second fastener hole,
wherein each screw includes an outer surface comprising a material that allows bone ingrowth into the material.

23. The device of claim 1 wherein:
the first section includes a first fastener hole and a second fastener hole, the first fastener hole of the first section having a central axis angled with respect to a central axis of the second fastener hole of the first section.

24. The device of claim 23 wherein:
the central axis of the first fastener hole of the first section is angled toward the central axis of the second fastener hole of the first section.

25. The device of claim 23 wherein:
the second section includes a first fastener hole and a second fastener hole, the first fastener hole of the second section having a central axis angled with respect to a central axis of the second fastener hole of the second section.

26. The device of claim 25 wherein:
the central axis of the first fastener hole of the second section is angled toward the central axis of the second fastener hole of the second section.

27. The device of claim 1 wherein:
the first section is twisted and the second section is twisted such that a first transverse line on the inner surface of the first section conforms to an outer surface of the T12 human vertebra and a second transverse line on the inner surface of the second section conforms to an outer surface of the L2 human vertebra when the plate is placed in contact with the spine of a patient.

28. The device of claim 27 wherein:
the first section is twisted and the second section is twisted such that a third transverse line on the inner surface between the first transverse line and the second transverse line conforms to an outer surface of the L1 human vertebra when the plate is placed in contact with the spine of a patient.

29. The device of claim 1 wherein the device is a thoracolumbar fixation device.

30. A method for the treatment of spinal instability, the method comprising: attaching the first section of the device of claim 1 to a first vertebra; and attaching the second section of the device of claim 1 to a second vertebra.

* * * * *

UNITED STATES PATENT AND TRADEMARK OFFICE
CERTIFICATE OF CORRECTION

PATENT NO. : 8,551,145 B2
APPLICATION NO. : 12/096959
DATED : October 8, 2013
INVENTOR(S) : Paul M. Huddleston, III It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1338 days.

Signed and Sealed this

Fifteenth Day of September, 2015

Michelle K. Lee
*Director of the United States Patent and Trademark Office*